United States Patent
Goldsmith et al.

(10) Patent No.: US 7,939,252 B2
(45) Date of Patent: May 10, 2011

(54) DIRECT QUANTIFICATION OF GENE EXPRESSION USING CAPILLARY ELECTROPHORESIS WITH LASER-INDUCED FLUORESCENCE

(75) Inventors: Edie C. Goldsmith, Lexington, SC (US); Jack G. Goldsmith, Lexington, SC (US)

(73) Assignee: University of South Carolina SC (US)

( * ) Notice: Subject to any disclaimer, the term of this patent is extended or adjusted under 35 U.S.C. 154(b) by 1348 days.

(21) Appl. No.: 11/455,275

(22) Filed: Jun. 16, 2006

(65) Prior Publication Data
US 2006/0286552 A1    Dec. 21, 2006

Related U.S. Application Data

(60) Provisional application No. 60/691,557, filed on Jun. 17, 2005.

(51) Int. Cl.
*C12Q 1/00* (2006.01)
*G01N 33/48* (2006.01)
*C12M 1/00* (2006.01)

(52) U.S. Cl. .............................. 435/6; 435/283.1; 702/19

(58) Field of Classification Search ........................ None
See application file for complete search history.

(56) References Cited

OTHER PUBLICATIONS

Al-Mahrouki, et al., "Calibration-Free Quantitative Analysis Of mRNA," *Anal. Chem.* 77: 8027-8030 (2005).
Bodkin, et al., "Assessment of Sequence Relatedness Of Double-Stranded RNA Genes by RNA-RNA Blot Hybridization," *J. Virol. Methods*, 10: 45-52 (1985).
Casey, et al., "Rates Of Formation And Thermal Stabilities Of RNA:DNA And DNA:DNA Duplexes At High Concentrations Of Formamide," *Nucl. Acids Res.* 4: 1539-1552 (1977).
Espy, et al., "Real-time PCR In Clinical Microbiology: Applications For Routine Laboratory Testing," *Clin. Microbiol. Rev.* 19: 165-256 (2006).
Fasco, et al., "Competitive RNA-PCR by Capillary Electrophoresis and Laser-Induced Fluorescence (LIF) Detection for Quantitation of Cellular mRNA," Beckman Application Information, *Nucleic Acids* A1788A: 1-5 (1994).
Ferri, et al., "Role of Discoidin Domain Receptors 1 and 2 In Human Smooth Muscle Cell-Mediated Collagen Remodeling," *Am. J. Pathol.* 164: 1575-1585 (2004).
Han, et al., "Monitoring Differential Synthesis Of RNA In Individual Cells By Capillary Electrophoresis," *Anal. Biochem.* 302: 136-143 (2002).
Han, et al., "In situ Sampling And Separation Of RNA From Individual Mammalian Cells," *Anal. Chem.* 72: 4073-4079 (2000).
Kolesar, et al., "Direct Quantification Of HIV-1 RNA By Capillary Electrophoresis With Laser-Induced Fluorescence," *J Chromatogr. B*, 697: 189-194 (1997).
Lai, et al., "Structure And Expression Of The Tyro 10 Receptor Tyrosine Kinase," *Oncogene*, 9: 877-883 (1994).
Odin, et al., "Rapid Method For Relative Gene Expression Determination In Human Tissues Using Automated Capillary Gel Electrophoresis And Multicolor Detection," *J. Chromatogr. B*, 734: 47-53 (1999).
Richards, et al., "Analysis Of Leptin Gene Expression In Chickens Using Reverse Transcription Polymerase Chain Reaction And Capillary Electrophoresis With Laser-Induced Fluorescence Detection," *J. Chromatogr. A*, 853: 321-335 (1999).
Sobczak, et al., "RNA Structure Analysis Assisted By Capillary Electrophoresis," *Nucl. Acids Res*, 30: e124 (2002).
van Eekelen, et al., "Quantitative Analysis Of Cytokeratin 20 Gene Expression Using RT-PCR And Capillary Electrophoresis With Fluorescent DNA Detection," *Clin. Biochem*, 33: 457-464 (2000).
Zabzdyr, et al., "A Qualitative Look At Multiplex Gene Expression Of Single Cells Using Capillary Electrophoresis," *Electrophoresis*, 26: 137-145 (2005).

*Primary Examiner* — Eric S Dejong
(74) *Attorney, Agent, or Firm* — Ballard Spahr LLP

(57) ABSTRACT

Provided is a method for direct quantification of gene expression using capillary electrophoresis with laser-induced fluorescence to measure RNA in a sample. Also provided is a method of diagnosing a disease in a subject, wherein the disease is caused by increased or decreased expression of a causative gene.

16 Claims, 5 Drawing Sheets

DIRECT QUANTIFICATION OF GENE EXPRESSION USING CAPILLARY ELECTROPHORESIS WITH LASER-INDUCED FLUORESCENCE

CROSS REFERENCE TO RELATED APPLICATIONS

This application claims priority to U.S. provisional application No. 60/691,557 filed on Jun. 17, 2005. The aforementioned application is herein incorporated by this reference in its entirety.

This invention was made with government support under Grants HL73937 and P20-RR16434 awarded by the National Institutes of Health. The government has certain rights in the invention.

BACKGROUND OF THE INVENTION

1. Field of the Invention

This invention relates generally to the field of measuring gene expression. Specifically, the present invention relates to a novel method for directly quantifying gene expression by measuring RNA using capillary electrophoresis with laser-induced fluorescence.

2. Background Art

The analysis of gene expression is a common experiment conducted routinely in many laboratories. Profiling gene expression provides valuable insight into genes involved in normal cell/tissue homeostasis, organism development and information about genes, that when their expression is up or down-regulated, lead to disease. A number of methods are currently employed to examine gene expression with the most common being Northern blotting, RNase Protection Assay (RPA), and Real-time Polymerase Chain Reaction (RT-PCR). Each of these methods has advantages and disadvantages mainly relating to sample size, cost, time involved, use of radioactivity, and transcript information and sensitivity which is estimated to vary from 10,000 copies of mRNA (Northern blotting) to theoretically one copy (RT-PCR). However, all of these methods suffer from one common drawback. None of them provides a direct concentration or copy number of the mRNA. Instead, these methods provide only a relative measure of change. In most cases, information regarding changes in gene expression obtained by these methods involves relative changes in the intensity (either from densitometric analysis or fluorescence) which is normalized to an internal control gene with the data being presented as percent or fold increase/decrease compared to control. If a quantitative answer is desired, a standard curve must be generated using known concentrations of RNA, which may be difficult if the RNA is in short supply and time consuming. Several studies have used CE-LIF to examine the expression of a number of genes including leptin (Richards et al., 1999), cytokeratin 20 (van Eekelen, 2000) and glyceraldehyde-3-phosphate dehydrogenase (Fasco et al., 1994); however, in each of these cases the RNA was first subjected to reverse transcription followed by PCR, and the PCR product was then analyzed by CE-LIF.

Northern blotting is currently the only method which will provide information regarding transcript size. Both Northern blotting and RPAs can distinguish multiple transcripts; however, in the case of RPAs, this requires careful probe design. Both methods typically involve the use of radioactivity for maximal sensitivity of target RNA and typically involve 3-5 days before the result is obtained. RT-PCR is the fastest method currently available to examine gene expression, but it provides no information regarding transcript size, and examination of multiple transcripts cannot be obtained from a single RT-PCR reaction. In addition, in RT-PCR the target RNA is first converted to complementary DNA (cDNA), and then the amplification of the DNA is what is measured. While Northern blotting and RPA both directly detect the target RNA, both of these methods require the use of an internal standard, and neither provides a direct quantitative measure of the target RNA. RT-PCR is an indirect measure which is subject to problems of non-specific amplification or genomic DNA contamination. This method also requires the use of a standard for normalization, and the user must keep in mind that not all RNAs/DNAs are amplified at the same rate.

What is needed is a method of quantifying gene expression that is fast, sensitive, non-radioactive, and direct. The novel method disclosed herein combines many of the desired features of the above mentioned techniques, such as information regarding size of target and number of transcripts, and eliminates the need for radioactivity. Moreover, the described method provides a direct, quantitative measure of a target RNA.

SUMMARY OF THE INVENTION

Capillary electrophoresis with laser induced fluorescence (CE-LIF) is a novel, method for the direct quantitation of gene expression. CE-LIF provides a fast, direct, sensitive and non-radioactive means to detect molecules, for example RNA. The method described herein is applicable to any RNA for which some sequence information is known and represents the first direct quantitation of gene expression in which the size of the target gene is obtained.

In accordance with the purposes of this invention, as embodied and broadly described herein, this invention, in one aspect, relates to a method of measuring an amount of ribonucleic acid (RNA), comprising (a) incubating an RNA sample with a fluorescently labeled RNA probe complementary to a sequence in a target RNA under conditions whereby the probe can hybridize to the target RNA to form an RNA:fluorescently labeled probe hybrid, (b) passing the RNA:fluorescently labeled probe hybrid through a capillary electrophoresis system, (c) detecting and recording changes in fluorescence as a peak as the RNA:fluorescently labeled probe passes through a detection window, and (d) determining an area under the peak, whereby the area under the peak indicates the amount of target RNA.

In another aspect, the invention relates to a method of diagnosing a disease in a subject, wherein the disease is characterized by an increased or decreased level of expression of a gene, comprising (a) determining a level of expression of the gene in the subject according to the disclosed method; (b) comparing the level of expression of the gene in the subject to a control level of expression of a gene from a subject without disease; (c) determining whether the level of expression from the subject in step (a) is increased or decreased compared to the control level, whereby an increased or decreased level of expression of the gene in the subject diagnoses the disease in the subject.

In another aspect, the invention relates to a method of diagnosing a bacterial disease or a viral disease in a subject, comprising identifying a target bacterial RNA or a target viral RNA in a sample from the subject according to the disclosed method, wherein the identification of the target bacterial RNA or the target viral RNA diagnoses the bacterial disease or the viral disease in the subject.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Figure 1:
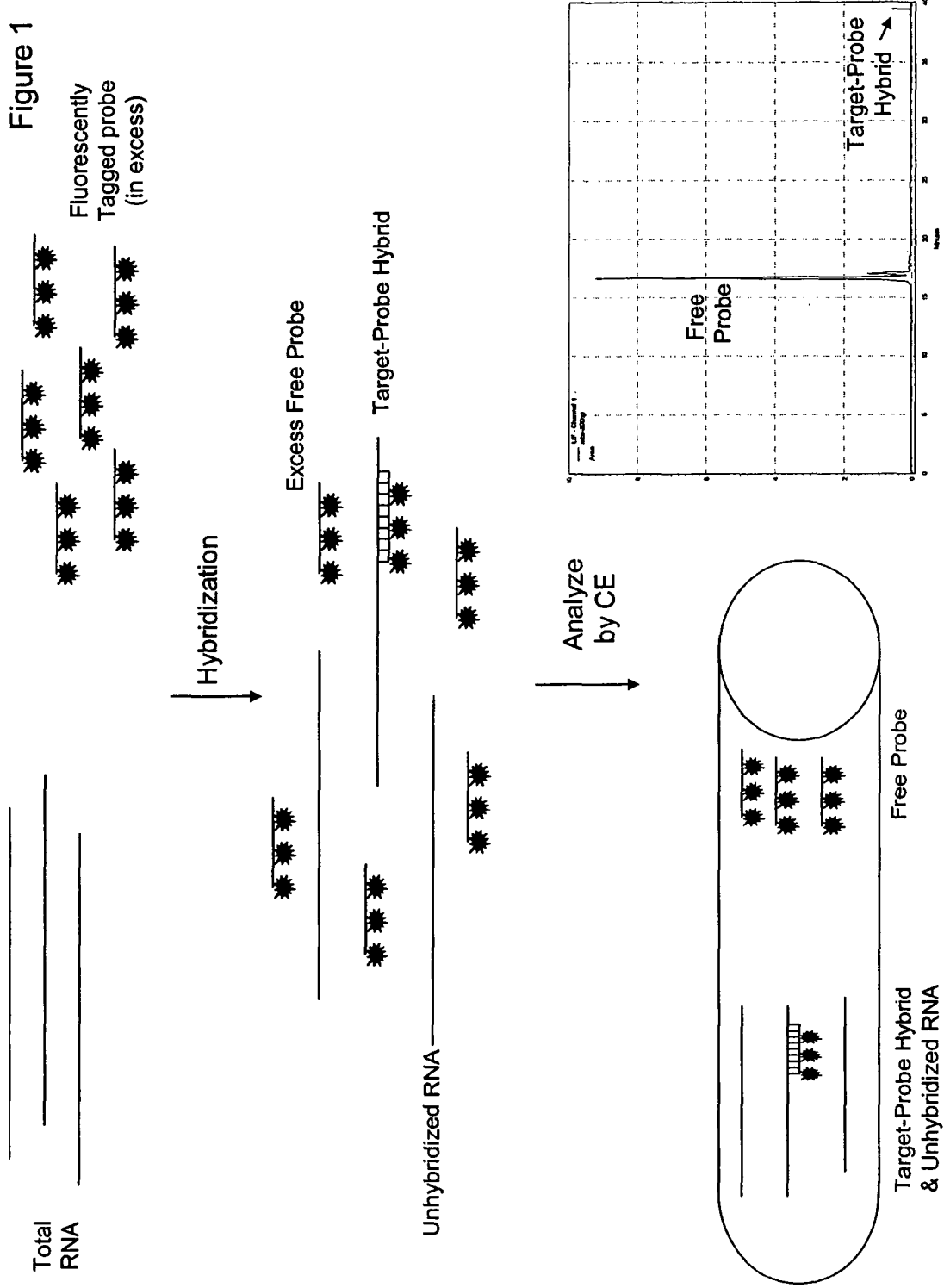
FIG. 1 shows a Schematic Using CE-LIF to Quantify RNA Expression. Fluorescently tagged riboprobe is added in excess to a sample of RNA and allowed to undergo hybridization of the labeled riboprobe to target RNA. The sample, containing free probe, unhybridized RNA and probe-target hybrids, is injected into a silica capillary containing a sieving matrix which will separate the various components of the hybridization reaction based upon their size. Using a fluorescence detector, as the various components of the hybridization reaction pass through the detection window, only those with the fluorescent molecule incorporated (free probe or probe-target hybrids) will be detected. Because the probe is much smaller than the target-probe hybrid, it passes through the detection window first followed at a later time by the target-probe hybrid.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific nucleic acid molecules, or to particular laser wavelengths, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to a ribonucleic acid includes mixtures of ribonucleic acid molecules, reference to a probe includes mixtures of two or more such probes, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings: "Optional" or "optionally" means that the subsequently described event or circumstance may or may not occur, and that the description includes instances where said event or circumstance occurs and instances where it does not. For example, the phrase "the sample optionally may contain more than one transcript" means that the sample may or may not contain more than one transcript and that the description includes both a sample containing one transcript and a sample containing more than one transcript.

Provided is a method of measuring an amount of RNA, comprising (a) incubating an RNA sample with a fluorescently labeled RNA probe complementary to a sequence in a target RNA under conditions whereby the probe can hybridize to the target RNA to form an RNA:fluorescently labeled probe hybrid, (b) passing the RNA:fluorescently labeled probe hybrid through a capillary electrophoresis system, (c) detecting and recording changes in fluorescence as a peak as the RNA:fluorescently labeled probe passes through a detection window, and (d) determining an area under the peak, whereby the area under the peak indicates the amount of target RNA. The disclosed method directly measures an amount of target RNA in an RNA sample. By "directly measures" is meant that because the target RNA is bound by the fluorescently labeled RNA probe (riboprobe), the fluorescence measured by the instrument is, in fact, arising from a species which contains the target RNA. The target RNA itself is not converted into any other molecule (i.e., there is no reverse transcription of the target RNA into a complementary DNA molecule). In addition, there are no intermediate steps in detection or conversion of the fluorescence to a numerical value. When the method is run using excess probe, the concentration of the target RNA of interest can be determined solely by using equation 1 as shown below. Thus, the disclosed method does not require the use of a standard curve or internal standard by which gene expression must be normalized. As shown below in the Examples, the direct determination of an RNA species can be made either through the use of a binding curve to determine the concentration of an RNA species or using the fluorescence from both the unhybridized free probe and bound target to calculate RNA concentration.

An RNA sample can contain RNA synthesized by methods known in the art. In another aspect, an RNA sample can contain RNA isolated from a cell, a tissue, or an organ from a subject. As used herein, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and more preferably, a human. In another aspect, an RNA sample can contain RNA from bacteria or viruses.

RNA probes, for example, SEQ ID NO:1 and SEQ ID NO:2, can be utilized as probes to detect a target RNA. For example, the RNA probe identified as SEQ ID NO:1 can be used to detect 28S rRNA. In another example, the RNA probe identified as SEQ ID NO:2 can be used to identify DDR2 mRNA. As used herein, the term "RNA probe" refers to a ribonucleic acid that selectively hybridizes under stringent conditions with a target RNA. A target RNA can be mRNA, rRNA, tRNA, miRNA, snRNA, or hnRNA. This hybridization must be specific. The degree of complementarity between the hybridizing ribonucleic acid probe and the target RNA sequence to which it hybridizes should be at least enough to exclude hybridization with a nucleic acid encoding an unrelated protein.

"Stringent conditions" refers to the hybridizatioin conditions used in the protocol. Stringent conditions are known to one of skill in the art. See, for example, Sambrook et al. (2001). An example of such conditions would be 40 mM PIPES, 1 mM EDTA, 0.4M NaCl, 80% formamide overnight at 42° C.

As used herein, a "fluorescently labeled probe" is a "riboprobe," an RNA probe that is complementary to a target RNA and contains a fluorophore that is directly incorporated into the probe during synthesis of the probe. In one aspect, a fluorophore can be directly incorporated into an RNA probe during a synthesis reaction known to a person of skill in the art. In another aspect, a plurality of fluorophores can be directly incorporated into a single RNA probe, providing greater sensitivity in detection.

To aid in detection and quantitation of nucleic acids amplified using the disclosed method, fluorophores (detection labels) can be directly incorporated into amplified nucleic acids or can be coupled to detection molecules. A fluorophore is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. A fluorescently labeled RNA probe (riboprobe) comprises a fluorophore selected from the group consisting of fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.18, CY5.18, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Phycoerythrin B, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are Alexa Fluor 488-5-UTP and BODIPY TR-14-UTP. Other preferred fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 mm), Cy5 (652 nm: 672 nm), Cy5.5 (682 nm; 703 nm) and Cy7 (755 mm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6- carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

A probe for interaction with a target gene in certain embodiments can be any size that supports the desired hybridization of the probe. A typical probe would be at least 20, 21, 22, 23, 24, 25, 26, 27, 28, 29, or 30 nucleotides long and can contain up to about 600 nucleotides. A probe, therefore, can contain from about 20 nucleotides to about 600 nucleotides, or any number of nucleotides in between. Thus, a probe can be 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, or 600 nucleotides long.

RNA:fluorescently labeled RNA probe hybrids and unbound fluorescently labeled RNA probes (riboprobes) can pass through a capillary electrophoresis system equipped with laser detection. In one aspect, a capillary electrophoresis system can be a microfluidic device, which is a device, on the order of millimeters or micrometers in size, designed to utilize volumes in the nanoliter (nL) or picoliter (pL) range. A microfluidic device is also referred to as a "lab on a chip."

In one aspect, a capillary electrophoresis system comprises one laser. In another aspect, a capillary electrophoresis system comprises a plurality of lasers. Examples of lasers include, but are not limited to, argon lasers, krypton lasers, dye lasers, and YAG lasers. For example, an argon laser emitting light with a wavelength from about 470 nm to about 510 nm can be used in a capillary electrophoresis system. In one aspect, the wavelength can be 488 nm. A second laser emitting light with a wavelength from about 610 nm to about 650 nm can also be used in a capillary electrophoresis system. In one aspect, the wavelength of light can be 635 nm.

A laser can be used to excite a fluorophore in RNA:fluorescently labeled RNA probe hybrids and in unbound fluorescently labeled RNA probes so that the fluorophore can emit energy at a specific wavelength (fluoresces) that can be detected as the labeled molecules pass through a detection window. Changes in fluorescence can be detected and shown in two peaks in an electropherogram. An electropherogram shows the data obtained from the CE-LIF instrument where signal is plotted vs. time. For example, an electropherogram can show fluorescence vs. time. In another aspect, an electropherogram can show absorbance vs. time for an ultraviolet (UV) detector or, in still another aspect, current vs. time for an electrochemical detector.

When fluorescence vs. time is shown, for example, one peak corresponds to the fluorescence emitted by RNA:fluorescently labeled RNA probe hybrids. The area under the first peak can be used to calculate the amount of target RNA in the RNA sample. A second peak corresponds to unhybridized (free) fluorescently labeled RNA probes (riboprobes).

An amount of target RNA, for example mRNA, in an RNA sample can be calculated using either one of the following two equations:

(1): Using Equation 1 below where [probe] is the concentration of fluorescently labeled RNA probe used in the hybridization reaction and $A_{target}$ and $A_{probe}$ are the area under the curve for the target RNA:fluorescently labeled RNA probe hybrid peak and the unhybridized (free) fluorescently labeled RNA probe peak, respectively, the concentration of mRNA, [mRNA], in the sample can be calculated. The concentration is in mole of RNA per liter of solution. The amount of RNA is the mass of RNA present (in grams or converted to micrograms, nanograms, or even picograms). This can be obtained from the concentration by multiplying the volume of sample present (expressed in liters) and then multiplying by the molar mass of the target RNA.

$$[mRNA] = [\text{probe}] \times \frac{A_{target}}{A_{target} + A_{probe}} \quad \text{Equation 1}$$

(2): Multiple hybridization reactions are conducted in which the amount of RNA remains constant, but the mass/concentration of fluorescently labeled RNA probe is varied, the resulting area under the curve measured for the target RNA:fluorescently labeled RNA probe hybrid peak is plotted versus mass of fluorescently labeled RNA probe and fit to the following Equation 2:

$$\text{Area} = Area_{max} \times \frac{Mass_{probe}}{K_d + Mass_{probe}} \quad \text{Equation 2}$$

in which $K_d$ equals the mass of fluorescently labeled RNA probe needed to reach half saturation of the target RNA by the probe. $Mass_{probe}$ is the mass of fluorescently labeled RNA probe used in the hybridization reaction, and $Area_{max}$ is the maximum area obtained when all of the target mRNA is bound by the fluorescently labeled RNA probe. The amount of target RNA present can be calculated from the $K_d$ value obtained from Equation 2 using the following expression:

$$massRNA = 2 \times K_d \times \left( \frac{\text{molar mass target } RNA}{\text{molar mass probe}} \right)$$

The mass, in grams, or 1 mole of the target RNA can be calculated by multiplying the number of bases in the target RNA by 330 grams per mole (for each base). The molar mass of the fluorescently labeled RNA probe is found the same way.

An amount of target RNA measured by the disclosed method can measure gene expression in a cell, a tissue, or an organ of a subject. In one aspect, measuring an amount of a target messenger RNA (mRNA) being transcribed for a particular protein, in a sample from a cell or tissue from a subject, provides information regarding gene expression. Further, the disclosed method discriminates between multiple transcripts of a gene. Moreover, the disclosed method can simultaneously detect multiple, distinct species of RNA. Because each target RNA:fluorescently labeled probe hybrid will have a distinct mass and conformation, it will need a characteristic amount of time to pass through the capillary and past the detection window. These differences between two unique target RNA:fluorescently labeled probe hybrids allows for them to be separated from one another in the capillary and therefore pass by the detection window at different times, and are thus simultaneously detected in the same sample. At the same time, by using a multiple wavelength detector, it is also possible to use a fluorophore that only one of the lasers on the instrument can detect (e.g., 488 nm vs. 620 nm). A target RNA:fluorescently labeled probe hybrid formed from the probe will only be detectable by one particular laser on the system, and at the same time, a different target RNA:fluorescently labeled probe hybrid formed using a different fluorophore will only be detectable using a different laser. Because the lasers operate simultaneously, it is possible to detect as many unique RNA species as there are lasers of different wavelengths. This successful detection can occur regardless of whether there is any difference in the time it takes the target RNA:fluorescently labeled probe hybrids to travel to the detector window. Even if the various target RNA:fluorescently labeled probe hybrids arrive simultaneously at the detection window, they will be detected separately.

Also provided is a method of diagnosing a disease in a subject, wherein the disease is characterized by an increased or decreased level of expression of a gene, comprising (a) determining a level of expression of the gene in a subject according to the method disclosed herein, (b) comparing the level of expression of the gene in the subject from step (a) to a control level of expression of a gene from a subject without disease, (c) determining whether the level of expression from the subject in step (a) is increased or decreased compared to the control level, whereby an increased or decreased level of expression of the gene in the subject diagnoses the disease in the subject. Any disease in which sequence information is known for a causative gene can be diagnosed by the disclosed method. Examples of diseases that can be diagnosed according to the disclosed method include, but are not limited to, carcinomas; sarcomas; cancer of the lung, breast, stomach, colon, prostate, brain, skin, thyroid gland, ovary, and testis; lymphoma; heart disease; hypertension; autoimmune diseases; diabetes mellitus; arthritis; inflammatory bowel disease (IBD), such as ulcerative colitis and Crohn's disease; atherosclerosis; hypertriglyceridemia; HDL2 deficiency; obesity; bone disease; Huntington's disease; lysosomal storage disorders; Parkinson's Disease; scleroderma; and pancreatic disease.

Further provided is a method of diagnosing a bacterial disease or a viral disease in a subject, comprising identifying a target bacterial RNA or a target viral RNA in a sample from the subject according to the disclosed method, wherein the identification of the target bacterial RNA or the target viral RNA diagnoses the bacterial disease or the viral disease in the subject. Examples of bacterial and viral diseases include, but are not limited to, bacterial and viral meningitis; infections caused by *Staphylococcus aureus, Escherichia coli, Streptococcus pneumoniae*, and Group B *Streptococcus*; HIV; SARS; tuberculosis; influenza; Hepatitis A; Hepatitis B; Hepatitis C; and Hepatitis E.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Preparation of Fluorescently Labeled Riboprobes. Fluorescently labeled 28S and DDR2 riboprobes, SEQ ID NO:1 and SEQ ID NO:2, respectively, were prepared using the pTRI-RNA-28S plasmid (Ambion) and a fragment of the rat DDR2 gene generated by RT-PCR using primers DDR2-6 (5'-AATGATCCCGATTCCCAGAATG-3') (SEQ ID NO:3) and DDR2-15 (5'-TCCCATGTCGGTTACGCCAG-3') (SEQ ID NO:4) and cloned into the pCRII vector (Invitrogen). In vitro transcription of both plasmids to produce riboprobe was accomplished using the MAXIscript in vitro transcription kit (Ambion). Briefly, 1 µg of linearized plasmid DNA was combined with 2 µl 10× Transcription buffer, 10 µl nuclease-free water, 1 µl each of 10 mM ATP, CTP, GTP, 0.6 µl 10 mM UTP, 0.4 µl 1 mM Alexa Fluor 488-5-UTP (28S and DDR2) or 0.4 µl BODIPY TR-14-UTP (28S; Molecular Probes) and 15 U/ml T7 or SP6 RNA Polymerase. To allow for sizing of RNA species during capillary electrophoresis, molecular weight makers were transcribed and labeled as described above with Alexa Fluor 488-5-UTP using the Century Marker Template (Ambion). The reaction was incubated 16-18 hours in a 37° C. water bath followed by treatment with DNase I (15 min, 37° C.) to digest plasmid DNA. Unincorporated nucleotides were removed using a Micro Bio-Spin 30 chromatography column (BioRad) and the concentration of the probe determined spectrophotometrically using absorbance at 260 nm. Quality and purity of synthesized probe was evaluated by denaturing agarose gel electrophoresis and capillary electrophoresis as described below.

Hybridization of Fluorescently tagged Riboprobe to Total RNA. To determine whether a specific RNA could be detected in a total RNA sample using CE-LIF, 488-28S riboprobe was hybridized to 5 µg and 10 µg of total RNA. Total RNA was isolated from 3-4 day neonatal rat hearts using RNA STAT-60 (Tel-Test) according to the manufacturer's directions and the concentration determined by absorbance at 260 nm. RNA was combined with 488-28S riboprobe and precipitated at −20° C. for 30 min using 5M $NH_4OAc$ and 95% EtOH. The precipitated product was subjected to centrifugation at 14,000 rpm for 15 min and the resulting pellet air dried. The pellet was resuspended in hybridization buffer (40 mM PIPES, 1 mM EDTA, 0.4M NaCl, 80% formamide), boiled for 3-4 min and incubated overnight at 42° C. The hybridized sample was re-precipitated as described above and the resulting pellet resuspended in 10 µl of DEPC-water. Simultaneous hybridization of both 488-DDR2 and Bodipy-28S probes was carried out as described above. Samples were placed in the P/ACE MDQ instrument and maintained at 4° C. until injection.

Capillary Electrophoresis with Laser-Induced Fluorescence. Fluorescent riboprobes were further analyzed by CE-LIF using a Beckman P/ACE MQD capillary electrophoresis system equipped with 488 nm and 635 nm lasers. Experiments were conducted using a 50 µm i.d. uncoated silicon capillary (Beckman) with an effective length of 28 cm and a total length of 40 cm. Prior to initial use, the capillary was conditioned by alternating pressure rinses (20 p.s.i) with methanol, 1N HCl, de-ionized water, 0.1N NaOH and 1×TBE (0.1M Tris pH 8.3, 0.1M Boric acid, 2 mM EDTA). Size separation of migrating species was accomplished using a previously described hydroxypropylmethylcellulose (HPMC) matrix (Han and Lillard, 2000) composed of 1% HPMC (MW ~10,000), 0.5% poly(vinylpyrrolidone) (MW ~1,000,000) and 6% mannitol in 1×TBE. Immediately prior to use the HPMC matrix was passed through a 0.45 µm filter followed by sonication to remove air bubbles. Ten second pressure injections (0.5 p.s.i.) were used to introduce sample into the capillary, and electrophoretic separation was accomplished using 8.0 kV constant voltage, reverse polarity and 1×TBE buffer for 40 min. To quantify the level of gene expression, the area under the curve representing the target RNA bound to the fluorescent probe was determined using Beckman 32Karat software.

Results

Overview of RNA quantitation using CE-LIF. Fluorescently tagged riboprobe is prepared against the target RNA and hybridized, in excess, to total RNA. Using an RNA probe instead of a DNA probe takes advantage of the increased stability of RNA-RNA hybrids compared to RNA-DNA hybrids (Bodkin and Knudson, 1985; Casey and Davidson, 1977). The hybridization reaction is then applied to a silicon capillary filled with a sieving matrix, and under constant voltage, the unhybridized (free) probe, which is smaller than the hybridized target, migrates faster passing through the detection window first followed by the target RNA:fluorescently labeled probe. The resulting electropherogram thus provides not only quantitative information regarding the abundance of the target species (obtained by measuring the area under the curve) but also will reveal if multiple transcripts of a target are also present.

Figure 2:
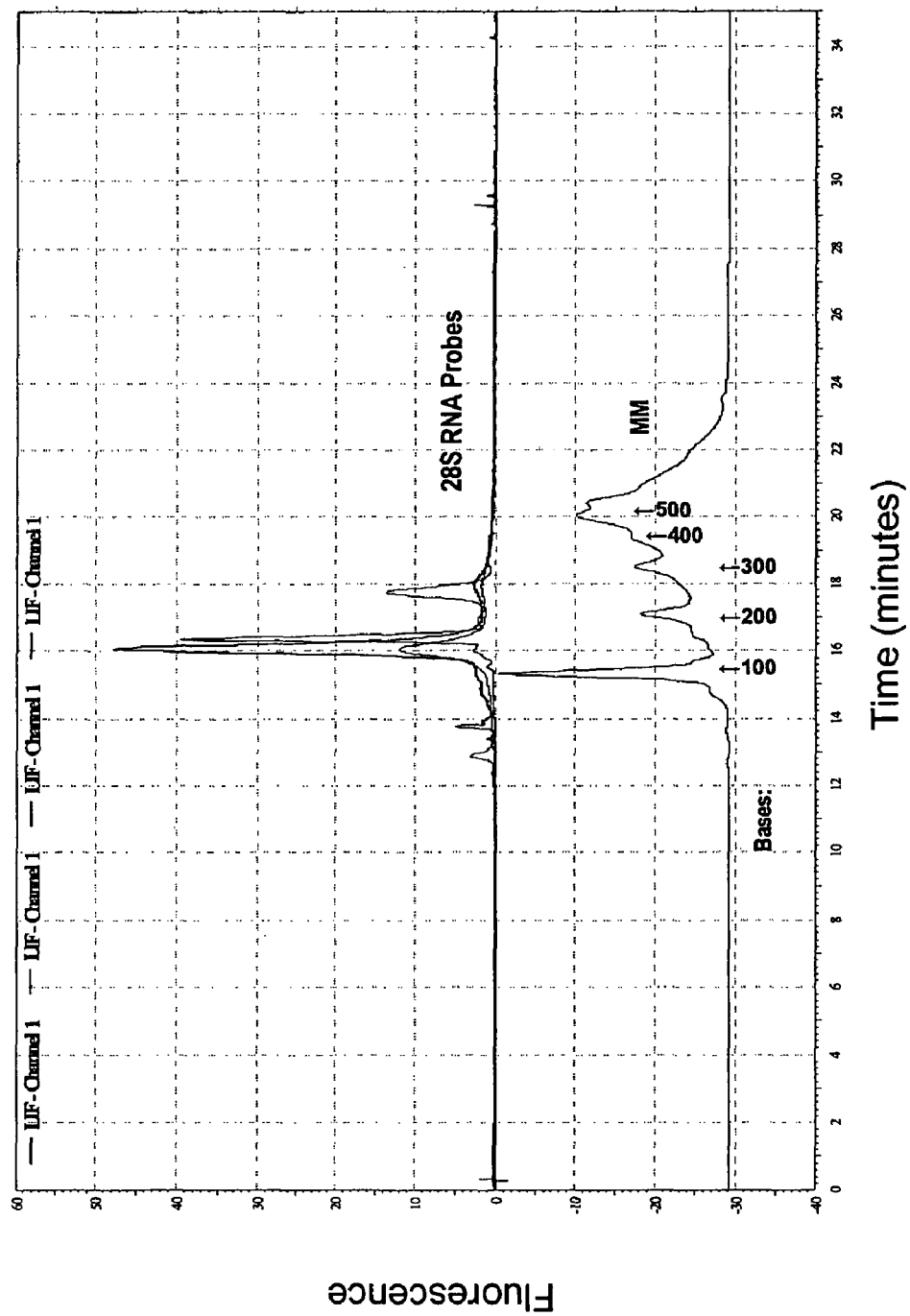
FIG. 2 shows Characterization of Fluorescently labeled 28S Probe. Multiple electropherograms representing independent probe synthesis reactions have been overlaid and are shown in the upper portion of this figure with a fluorescently labeled molecular weight marker shown in the lower portion. In each of the probe reactions, a major peak migrating between 15 and 17.5 minutes migrated at the correct time compared to the molecular weight markers to be 155 bases in length.

Characterization of Fluorescent Riboprobes. After removal of unincorporated nucleotides, riboprobes were examined both by agarose gel electrophoresis and CE-LIF to check probe purity and integrity. FIG. 2 shows electropherograms from three representative 488-28S probe synthesis reactions along with the fluorescently transcribed molecular weight markers. Each sample contained 50 ng/µl of probe which corresponds to approximately 15 nl injected volume containing 0.78 ng of riboprobe. For each probe reaction, one major peak was detected which migrated between 15 and 17.5 minutes. Using the T7 RNA polymerase to transcribe the TRI-RNA-28S plasmid, a 155 base riboprobe is produced. The fluorescent riboprobe produced in these reactions migrates between the 100 and 200 base RNA markers as would be expected (FIG. 2). Analysis by denaturing agarose gel electrophoresis also showed a single band whose migration was consistent with a riboprobe of this size. Identical results were obtained when the 28S riboprobe was produce with the Bodipy-UTP. Similar analysis was conducted with the 488-DDR2 probe, demonstrating that upon transcription with SP6 polymerase, a 492 base riboprobe was produced.

Figure 3:
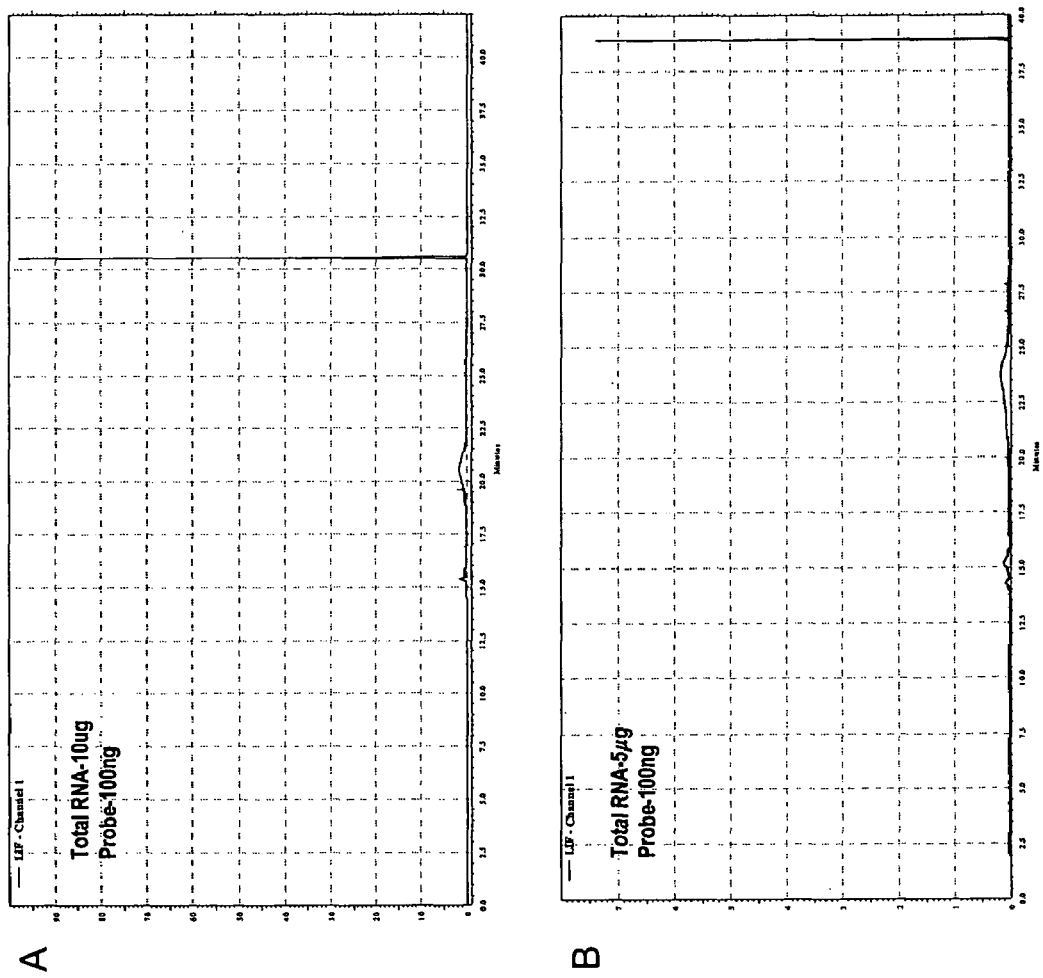
FIGS. 3A and 3B show Post-hybridization Electropherograms. Representative electropherograms are shown for the hybridization of 10 µg (A) and 5 µg (B) of total RNA with the 488-28S probe. In each case, a small fluorescent peak corresponding to unhybridized, free probe migrating around 15 minutes and a second larger peak, representing the 28S RNA-488-28S probe hybrid was also detected. The difference in migration time of the 28S RNA-488-28S probe hybrid is attributed to different conformations of the target-probe hybrid which may form during the hybridization process.

Hybridization of 10 µg and 5 µg of Total RNA to 488-28S Riboprobe. Representative electropherograms are shown for hybridizations of 5 µg and 10 µg of total RNA (FIGS. 3A and 3B). In all hybridization reactions, a single peak was observed; however, variability in migration time was noted. This is attributed to alterations in RNA-probe conformation during the hybridization process as other studies were done to confirm probe specificity, and previous work has shown that CE can distinguish changes in RNA conformation (Sobczak and Krzyzosiak, 2002).

Figure 4:
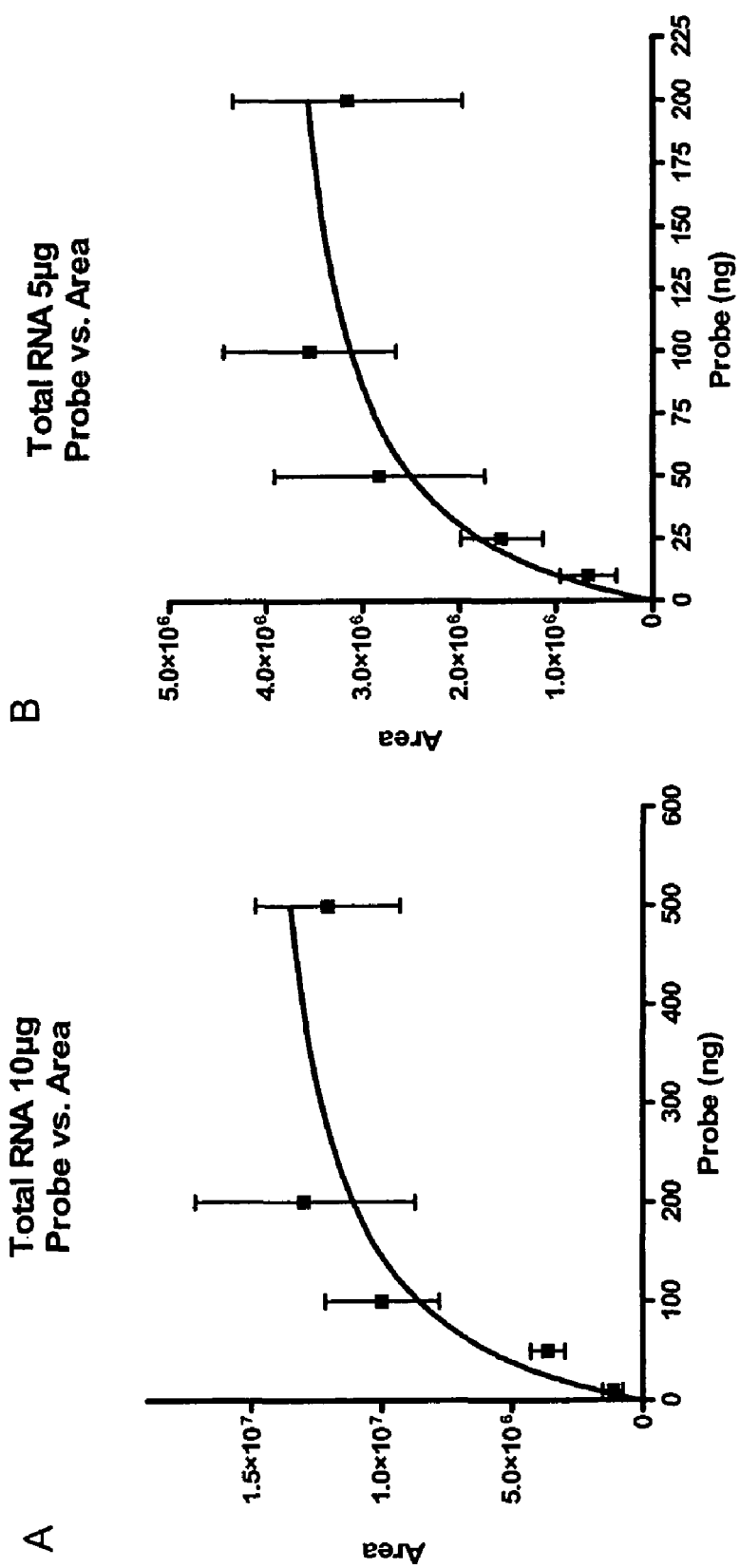
FIGS. 4A and 4B show Analysis of 488-28S probe binding to 28S RNA. Using a single site binding model, binding curves were generated for 10 µg (A) and 5 µg (B) of total RNA hybridized to 488-28S probe. Both curves demonstrate the hybridization reactions reached saturation at sufficient probe concentrations, with $K_d$ values of 84 ng (10 µg of RNA) and 33 ng (5 µg of total RNA) for the probe target sequence. Because $K_d$ is the half-maximal concentration of target RNA sequence, $2K_d$ represents the amount of target sequence present at saturation, corresponding to 168 ng and 66 ng, respectively.

Determination of 28S rRNA present in 5 µg and 10 µg RNA samples. To determine the amount of 28S rRNA present in 5 µg and 10 µg of total RNA and at what point the probe was present in excess, binding curves were constructed from experiments in which the amount of total RNA in the hybridization reaction remained constant and the amount of 488-28S riboprobe was varied. Given a 1:1 binding between labeled riboprobe and target RNA, the area under the peak (denoted as hybridized product in FIGS. 3A and 3B) represents the amount of target RNA present. The graphs in FIGS. 4A and 4B show peak area plotted versus amount of probe and are fit to the equation describing a single site binding event. It is evident from these plots that saturation of target RNA occurred and the resulting $K_d$ values obtained were 84 ng and 33 ng for 10 µg and 5 µg of total RNA, respectively. Because $K_d$ represents the half-maximal concentration of probe, this would correspond to 168 ng and 66 ng of 28S probe present in 10 µg and 5 µg of total RNA.

Figure 5:
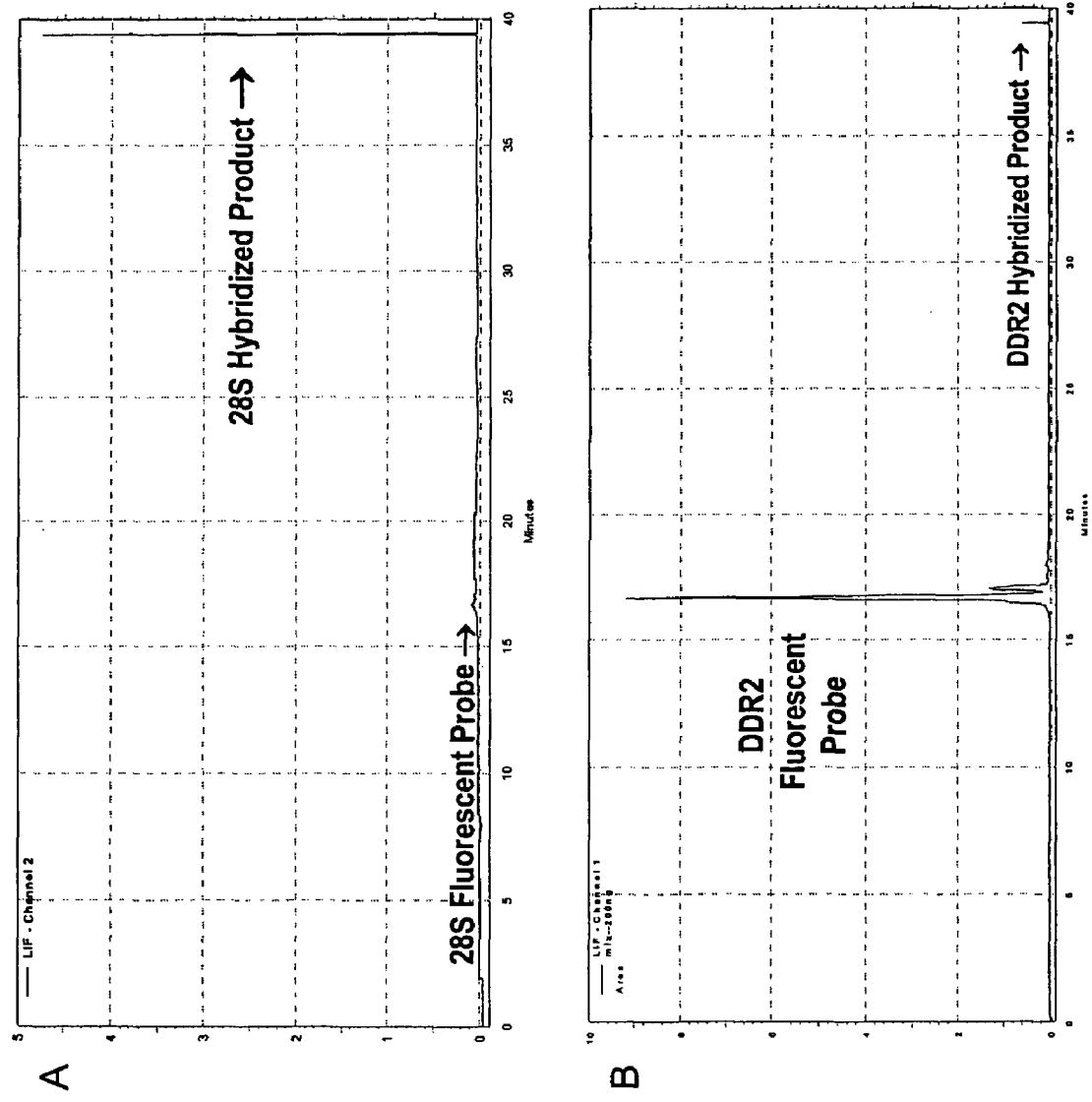
FIGS. 5A and 5B show Simultaneous Multiple Gene Expression Analysis using CE-LIF. Representative electropherograms are shown for a single sample hybridized simultaneously with (A) Boidpy-28S probe and (B) 488-DDR2 probe. Note the significant difference in the target-probe hybrid peaks for the 28S and DDR2 probes showing that the mRNA for DDR2 is expressed at a much lower level compared to 28S in a sample in which the same amount of both probes is used. The large free DDR2 probe peak indicates that this hybridization reaction was conducted at saturating levels of DDR2 probe.

Simultaneous Detection of Multiple Genes using CE-LIF. While the analysis of a single gene can provide valuable information regarding changes in expression, the simultaneous quantitation of multiple transcripts is advantageous, especially if the amount of RNA is limited. To determine whether CE-LIF could be used to distinguish multiple target genes, 488-DDR2 and Bodipy-28S riboprobes (200 ng each) were prepared and simultaneously hybridized to 10 µg of total RNA. Representative electropherograms are shown in FIGS. 5A and 5B. Given the separation in emission wavelengths between the 488 and Bodipy fluorphores (520 nm and 625 nm), no bleed through fluorescence was anticipated, and electropherograms collected on unhybridized (free) probe in both fluorescence channels demonstrated this was the case. A single DDR2 transcript which migrated at 39.5 minutes was detected. This is in agreement with literature reports for only one transcript of DDR2 being present in the heart (Lai and Lemke, 1994). Area under the curve analysis using the equation $[mRNA]=[probe](A_{hybrid})/(A_{hybrid}+A_{probe})$ (Al-Mahrouki and Krylov, 2005) revealed that the DDR2 mRNA was present at a concentration of 0.26±0.01 ng/µl. The DDR2 mRNA has been detected as single or multiple transcripts ranging in size from 4.5 kb to 9.5 kb in length depending upon the tissue source of the RNA (Lai and Lemke, 1994; Ferri et al., 2004). Given the size of the riboprobe used in these experiments (492 bases), the DDR2 mRNA would essentially co-migrate with the 28S RNA (~4.7 kb RNA plus 155 base probe) as shown in FIGS. 5A and 5B. This result demonstrates not only the ability to quantitate multiple RNA species simultaneously but also to resolve multiple species with similar sizes.

Throughout this application, various publications are referenced. The disclosures of these publications in their entireties are hereby incorporated by reference into this application in order to more fully describe the state of the art to which this invention pertains.

REFERENCES

Bodkin, D. K. & Knudson, D. L. Assessment of sequence relatedness of double-stranded RNA genes by RNA-RNA blot hybridization. J. Virol. Methods 10, 45-52 (1985).

Casey, J. & Davidson, N. Rates of formation and thermal stabilities of RNA:DNA and DNA:DNA duplexes at high concentrations of formamide. Nucl. Acids Res. 4: 1539-1552 (1977).

Espy, M J. et al. Real-time PCR in clinical microbiology: applications for routine laboratory testing. Clin. Microbiol. Rev. 19, 165-256 (2006).

Fasco, M. J., Treanor, C. P., Spivack, S., Figge, H. L. & Kaminsky, L. S. 1994. Beckman Application Information, Nucleic Acids A1788A: 1-5.

Ferri, N., Carragher, N. O. & Raines, E. W. Role of Discoidin Domain Receptors 1 and 2 in human smooth muscle cell-mediated collagen remodeling. Am. J. Pathol. 164, 1575-1585 (2004).

Han, F. & Lillard, S. J. In situ sampling and separation of RNA from individual mammalian cells. Anal. Chem. 72, 4073-4079 (2000).

Han, F. & Lillard, S. J. Monitoring differential synthesis of RNA in individual cells by capillary electrophoresis. Anal. Biochem. 302, 136-143 (2002).

Kolesar, J. M., Allen, P. G. & Doran, C. M. J. Direct quantification of HIV-1 RNA by capillary electrophoresis with laser-induced fluorescence. Chromatogr. B 697, 189-194 (1997).

Lai, C. & Lemke, G. Structure and expression of the Tyro 10 receptor tyrosine kinase. Oncogene 9, 877-883 (1994).

Odin, E., Wettergren, Y., Larsson, L., Larson, P. A. & Gustavsson, B. Rapid method for relative gene rexpression determination in human tissues using automated capillary gel electrophoresis and multicolor detection. J. Chromatogr. B 734, 47-53 (1999).

Richards, M. P., Ashwell, C. M. & McMurtry, J. P. Analysis of leptin gene expression in chickens using reverse transcription polymerase chain reaction and capillary electrophoresis with laser-induced fluorescence detection. J. Chromatogr. A 853, 321-335 (1999).

Sobczak, K. & Krzyzosiak, W. J. RNA structure analysis assisted by capillary electrophoresis. Nucl. Acids Res 30 e124 (2002).

van Eekelen, J. A. M., Shammas, F. V., Wee, L., Heikkila, R. & Osland, A. Quantitative analysis of Cytokeratin 20 gene expression using RT-PCR and capillary electrophoresis with fluorescent DNA detection. Clin. Biochem. 33, 457-464 (2000).

Al-Mahrouki, A. A. & Krylov, S. N. Calibration-free quantitative analysis of mRNA. Anal. Chem. 77, 8072-8030 2005.

Zabzdyr, J. L & Lillard, S. J. A qualitative look at multiplex gene expression of single cells using capillary electrophoresis. Electrophoresis 26, 137-145 (2005).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of measuring an amount of target ribonucleic acid (RNA), comprising
   a. incubating an RNA sample with one or more fluorescently labeled RNA probes complementary to one or more respective target RNA sequences in the RNA sample under conditions whereby the one or more probes can hybridize to the one or more respective target RNAs to form one or more RNA:fluorescently labeled probe hybrids;
   b. passing the RNA sample comprising the one or more RNA:fluorescently labeled probe hybrids through a capillary electrophoresis system;
   c. detecting and recording fluorescence as one or more peaks as the RNA sample comprising the one or more RNA:fluorescently labeled probe hybrids passes through a detection window, wherein each of the one or more RNA:fluorescently labeled probe hybrids generates its own peak; and
   d. determining an area under each peak for the respective RNA:fluorescently labeled probe hybrid whereby the area under each peak corresponds to the amount of respective target RNA in the RNA sample, wherein no target RNA is reverse transcribed during steps (a)-(d).

2. The method of claim 1, wherein RNA is isolated from a cell, a tissue, or an organ of a subject.

3. The method of claim 1, wherein the one or more fluorescently labeled RNA probes are made by incorporating a fluorophore into the one or more RNA probes during a synthesis reaction.

4. The method of claim 2, wherein the amount of target RNA measures gene expression in the cell, the tissue, or the organ.

5. The method of claim 1, wherein the one or more peaks of step (c) correspond to one or more transcripts of a gene.

6. The method of claim 1, wherein the one or more peaks of step (c) correspond to distinct species of RNA.

7. The method of claim 1, wherein the fluorescently labeled probe comprises a fluorophore selected from the group consisting of Alexa Fluor 488-5-UTP, BODIPY TR-14-UTP, fluorescein (5-carboxyfluorescein-N-hydroxysuccinimide ester), rhodamine (5,6-tetramethyl rhodamine), the cyanine dyes Cy3, Cy3.5, Cy5, Cy5.5 and Cy7, 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC).

8. The method of claim 1, wherein the one or more fluorescently labeled probes hybridize to RNA under stringent conditions.

9. The method of claim 1, wherein the capillary electrophoresis system is a microfluidic device.

10. The method of claim 1, wherein the capillary electrophoresis system is equipped with laser detection, comprising one or more lasers.

11. The method of claim 10, wherein a first laser is an argon laser having a wavelength from about 470 nm to about 510 nm.

12. The method of claim 11, wherein the wavelength is 488 nm.

13. The method of claim 10, wherein a second laser has a wavelength from about 610 nm to about 650 nm.

14. The method of claim 13, wherein the wavelength is 635 nm.

15. The method of claim 1, wherein the one or more peaks are recorded in an electropherogram.

16. A method of measuring an amount of target ribonucleic acid (RNA), comprising
   a. incubating an RNA sample with one or more fluorescently labeled RNA probes complementary to one or more respective target RNA sequences in the RNA sample under conditions whereby the one or more probes can hybridize to the one or more respective target RNAs to form one or more RNA:fluorescently labeled probe hybrids;
   b. passing the RNA sample comprising the one or more RNA:fluorescently labeled probe hybrids through a capillary electrophoresis system;
   c. detecting and recording fluorescence as one or more peaks as the RNA sample comprising the one or more RNA:fluorescently labeled probe hybrids passes through a detection window, wherein each of the one or more RNA:fluorescently labeled probe hybrids generates its own peak; and
   d. determining an area under each peak for the respective RNA:fluorescently labeled probe hybrid whereby the area under each peak corresponds to the amount of respective target RNA in the RNA sample, wherein no target RNA is reverse transcribed during steps (a)-(d), and wherein the amount of RNA is calculated from either the following equation (a):

$$[mRNA] = [\text{probe}] \times \frac{A_{\text{target}}}{A_{\text{target}} + A_{\text{probe}}}, \quad (a)$$

wherein [probe] is the concentration of fluorescently labeled RNA probe used in a hybridization reaction, wherein $A_{target}$ and $A_{probe}$ are the area under the curve for a target RNA:fluorescently labeled probe hybrid peak and an unhybridized probe peak respectively, whereby the concentration of mRNA, [mRNA], in the sample is calculated; or from the following equation (b):

$$\text{Area} = \text{Area}_{max} \times \frac{Mass_{probe}}{K_d + Mass_{probe}} \quad (b)$$

wherein $K_d$ equals the mass of a fluorescently labeled RNA probe needed to reach half saturation of a target RNA by the fluorescently labeled RNA probe, wherein $Mass_{probe}$ is the mass of a fluorescently labeled RNA probe used in a hybridization reaction, wherein $Area_{max}$ is the maximum area obtained when all of the target RNA is bound by the fluorescently labeled RNA probe, whereby the amount of target RNA present can be calculated from the $K_d$ value using the following expression:

$$massRNA = 2 \times K_d \times \left(\frac{\text{molar mass target } RNA}{\text{molar mass probe}}\right).$$

* * * * *

SEQUENCE LISTING

```
<160> NUMBER OF SEQ ID NOS: 4

<210> SEQ ID NO 1
<211> LENGTH: 115
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 1
ggauuggaca gagugcugcc agauuugggu cgagugcaag ggauaaucac ccacuuguua      60
gguugcgaac cacuuaagac gaaguguuac uauccuucuc ggcuguagcu uccua         115

<210> SEQ ID NO 2
<211> LENGTH: 413
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 2
uuacuagggc uaagggucuu acggagacca cgacgacgac gaggacgagu aggacccaag     60
acguuuucga guccaauuag gucgguauac agcgauagga gacccguaca guccuccggu    120
guaaggucua cuccuguagu gucgaaguuc agucaccagu cuuagguguc gacgguuuau    180
acccuccgac cugagacuuc uuccccuacc ucgaaccacg ggacucuaag gucacguugg    240
gcuacuggac uuccuuaaag acgucuaacu aaaugcuugg gaugugaaau agugagaaca    300
ccccuggguc ccugcgguac guccccagu accguaacuu aaacguggu acauguucua      360 guugauguca gcccuaccgu uggcgaccua gaggaccgca uuggcuguac ccu            413

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
```

```
aatgatcccg attcccagaa tg                                              22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 4
tcccatgtcg gttacgccag                                                 20
```